United States Patent [19]
Yoshinori

[11] Patent Number: 5,152,755
[45] Date of Patent: * Oct. 6, 1992

[54] TUBE ASSEMBLY WITH A BREAKAWAY PLUG

[75] Inventor: Minagawa Yoshinori, Fujinomiya, Japan

[73] Assignee: Terumo Kabushiki Kaisha, Tokyo, Japan

[*] Notice: The portion of the term of this patent subsequent to Apr. 10, 2007 has been disclaimed.

[21] Appl. No.: 460,051
[22] PCT Filed: Mar. 15, 1988
[86] PCT No.: PCT/JP88/00270
§ 371 Date: Feb. 22, 1990
§ 102(e) Date: Feb. 22, 1990
[87] PCT Pub. No.: WO89/00433
PCT Pub. Date: Jan. 26, 1989

[30] Foreign Application Priority Data

Jul. 16, 1987 [JP] Japan .................. 62-177900

[51] Int. Cl.⁵ .............................. A61M 25/00
[52] U.S. Cl. ..................... 604/256; 604/284; 604/905
[58] Field of Search ............ 604/148, 244, 246, 256, 604/280, 283–284, 905

[56] References Cited

U.S. PATENT DOCUMENTS

| | | |
|---|---|---|
| 3,368,560 | 2/1968 | Gewecke . |
| 4,228,835 | 10/1980 | Robinson et al. . |
| 4,294,247 | 10/1981 | Carter et al. ............ 128/214 D |
| 4,394,919 | 7/1983 | von Alven et al. . |
| 4,402,682 | 9/1983 | Garver, Sr. et al. ............ 604/111 |
| 4,636,204 | 1/1987 | Christopherson . |
| 4,899,903 | 2/1990 | Miyasaka et al. ............ 220/266 |
| 4,911,696 | 3/1990 | Miyasaka et al. ............ 604/244 |
| 4,915,704 | 4/1990 | Miyasaka et al. ............ 604/256 |

FOREIGN PATENT DOCUMENTS

| | | |
|---|---|---|
| 355160 | 2/1990 | European Pat. Off. . |
| 2449609 | 9/1980 | France . |
| 58-188456 | 11/1983 | Japan . |
| 8602905 | 5/1986 | PCT Int'l Appl. . |

Primary Examiner—C. Fred Rosenbaum
Assistant Examiner—C. Maglione
Attorney, Agent, or Firm—Frishauf, Holtz, Goodman & Woodward

[57] ABSTRACT

An assembly of a tube having a breakaway plug mounted on one opening thereof is provided. The plug includes a hollow cylindrical segment fixedly secured to the tube, a closing segment, and a frangible annular portion located in the hollow segment apart from the secured portion. The plug is formed of material having a Shore A hardness of 68–76 such that the plug can be torn off at the frangible portion by twisting. Since the plug of relatively flexible material having a Shore A hardness of 68 to 76 is attached to the tubular body, the gas tightness and intimate contact therebetween are substantially improved to minimize the risk of the plug being accidentally ruptured by an external force when the tubular body is not on use, while maintaining the ability of breakage of the plug when the tubular body is on use.

Preferably, there is provided a protector with such a hardness that it may not prevent breakage of the plug at the frangible portion for safeguard and easy breakage of the plug.

1 Claim, 5 Drawing Sheets

TUBE ASSEMBLY WITH A BREAKAWAY PLUG

BACKGROUND OF THE INVENTION

1. Field of the Invention

This invention relates to a tube assembly with a breakaway plug. More particularly, it relates to a tube assembly having a breakaway plug which is unlikely to be ruptured or contaminated before use.

2. Discussion of Prior Art

In some branch tubes such as four-way branch tubes for use in combination with blood collection bags, all the branches are not used at the same time, but they are used one by one in successive steps. To prevent the flow path from being contaminated from a branch which is not in use, the branch not in use should be completely sealed with a plug or a suitable closure. Upon use of the branch which has been sealed with a plug, it is necessary that the plug be readily broken and removed to open the associated branch to allow for connection to another member such as a tube having a puncture needle.

A variety of plugs which can be torn off have been proposed in the prior art. For example, T. Gewecke, U.S. Pat. No. 3,368,560 discloses an outlet fitting wherein a cap portion is united to a tubular portion by means of a relatively thin annular web. A finger tab depending from the cap portion is pulled whereupon a line of severance occurs in the area of the integral web.

This fitting is applicable as a plug on a branch of a four-way branch tube, but has a problem in operation. When the cap is pulled with a considerable force in an axial direction to cut the cap at the thin web, there occurs an impact of reaction At the instant of rupture, the operator would probably hit something at her elbow. Additionally, the cut edge would be brought in contact with something so that it might be contaminated.

C. Robinson et al, U.S. Pat. No. 4,228,835 discloses a breakaway cap comprising a ring having an open end and a closed end with a handle An annular grooved area is provided as a frangible connection between the open end portion and the closed end of the ring. When the handle is grasped and moved angularly, the ring will break at the frangible section to remove the handle from the ring. The cap is formed of a polyvinyl chloride having a hardness in the range of 85-100 as measured on the Shore A scale of a durometer.

This cap is also applicable as a plug on a branch of a four-way branch tube and considered as preventing the inadvertent reaction of breakage inevitable with the cap of Gewecke. The cap has a certain degree of hardness so that it is broken at the frangible section by moving the handle angularly. Since the plug or breakaway cap is united with the frangible section and a flexible tube is connected to the ring portion of the cap left after breakage, the ring portion of the cap must be utilized as a waist in bending the handle. For this reason, the cap is made of a material having a Shore A hardness of 85-100. Since the cap of this range of hardness is rather less flexible, it has problems in gas tightness, adherence to the branch or tubular body, and prevention of accidental rupture before it is desired to break the plug to open the flow path of the branch on use.

DISCLOSURE OF THE INVENTION

An object of the present invention is to provide a tube assembly having a breakaway plug which is mounted on a tubular body in an air-tight and intimate contact manner without the risk of being accidentally ruptured or contaminated during manufacture or transportation, but can be readily torn off upon use.

According to the present invention, there is provided a tube assembly comprising a tubular body of a relatively rigid material having at least two open ends, and a plug of a material having a Shore A hardness of from 68 to 76 mounted on one open end of the tubular body, the plug including (a) a hollow mount segment having an open end, a portion of the mount segment extending from its open end being fixedly secured to the one open end of the tubular body, (b) a closing segment axially connected to the mount segment, and (c) a frangible portion located axially outside the secured portion whereby the plug is breakable at the frangible portion and removable from the one open end of the tubular body.

Preferably, there is provided a protector with such a hardness that it may not prevent breakage of the plug at the frangible portion.

BRIEF DESCRIPTION OF THE DRAWINGS

The above and other objects, features, and advantages of the invention will be better understood by reading the following description taken in conjunction with the accompanying drawings, in which.

DESCRIPTION OF THE PREFERRED EMBODIMENT

The tube assembly of the present invention includes a tube body having at least two open ends. Any tubular body having at least two open ends between which a flow path extends may be employed. Although a commonly used four-way branch tube is referred to as a typical example in the following description, the present invention is not limited to the four-way branch tube. Among various medical tubes, four-way branch tubes are widely used in combination with blood collection bags.

Figure 1:
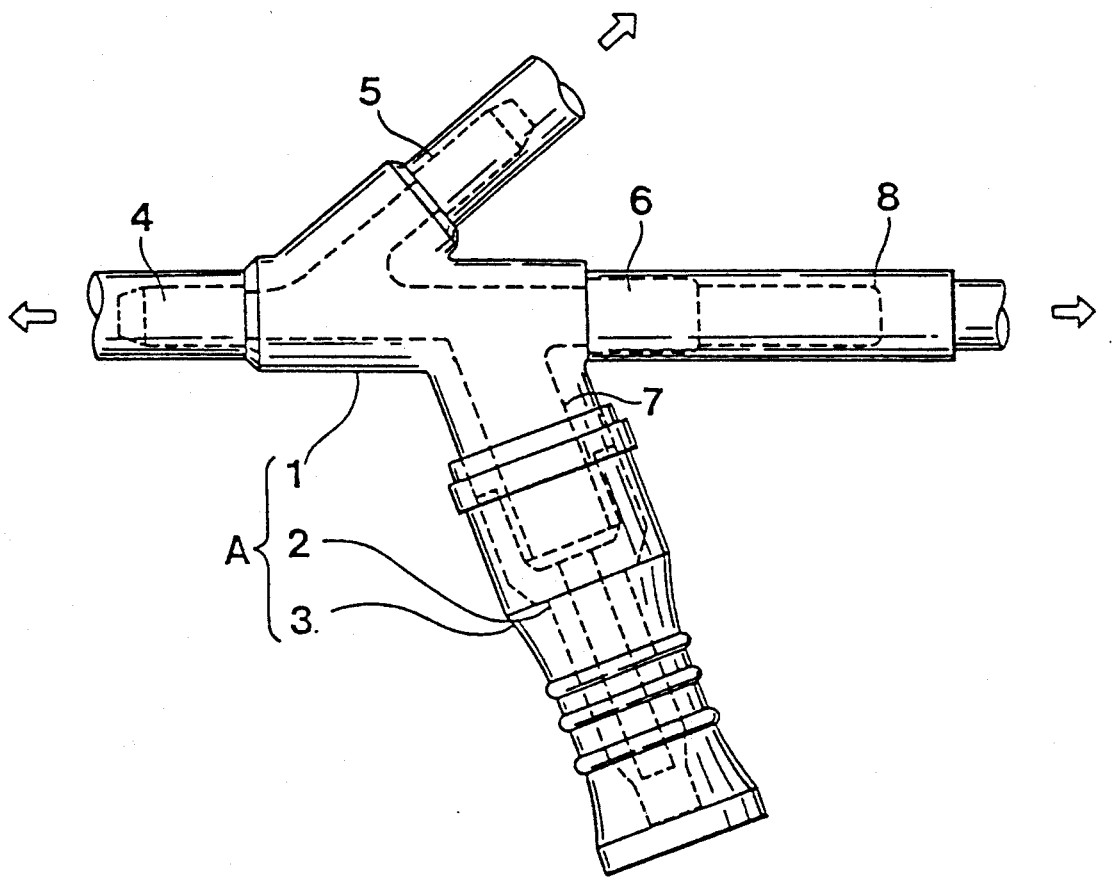
FIG. 1 is a partially cross-sectional plane view of a four-way branch tube with a breakaway plug according to one embodiment of the present invention.
Figure 4A:
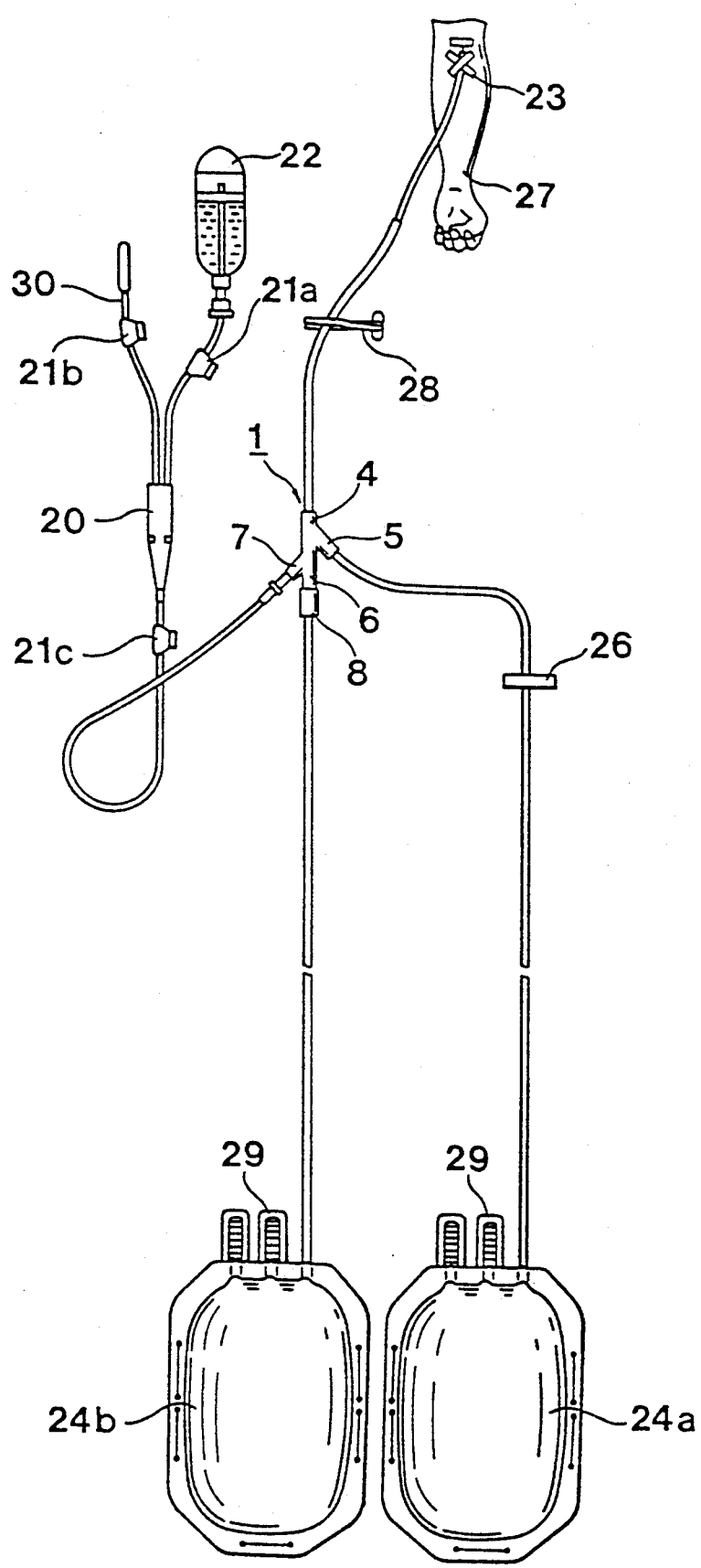
FIG. 4a and 4b illustrate a plasmapheresis system having the tube assembly of the invention incorporated therein.

FIG. 1 illustrates a four-way branch tube as one embodiment of the tube assembly of the present invention. The four-way branch tube with a breakaway plug generally designated at A includes a tubular body 1 having four openings, a plug 2 mounted on one opening of the tubular body 1, and a protector 3 fitted over the plug for protecting the plug. The tubular body 1 has one main tube and two branches connected thereto at an angle in a usual manner. The tubular body 1 has four openings, a first opening 4, a second opening 5, a third opening 6, and a fourth opening 7. For brevity of description, the first opening 4 is designated a proximal side, and the second, third and fourth openings 5, 6 and 7 are designated distal sides because the first opening 4 is connected to a blood collecting needle as shown in FIG. 4a. The distal end of the main tube or the third opening 6 is provided with a closure member 8 which normally closes the flow path, but is breakable to open the flow path. The feature of the present invention resides in the second branch defining the fourth opening 7 on which the plug 2 and the protector 3 are mounted.

Figure 3A:
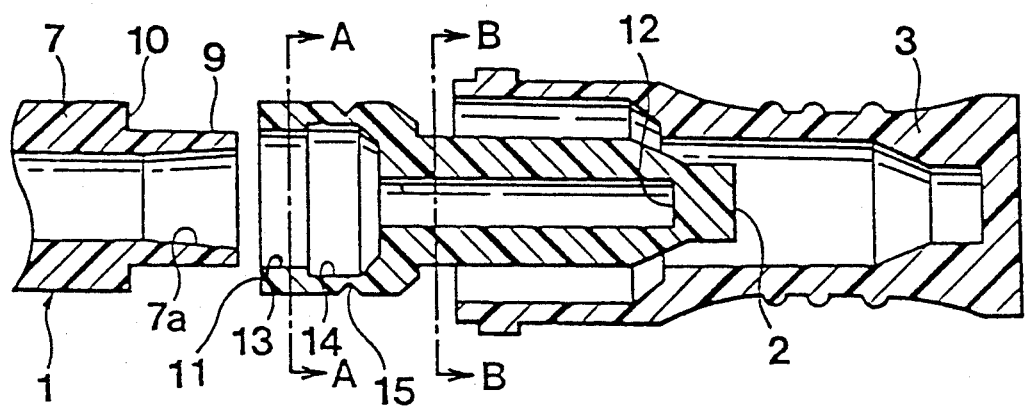
FIG. 3a and 3b are cross-sectional views of the plug taken along lines A—A and B—B in FIG. 2a, respectively.
Figure 3B:
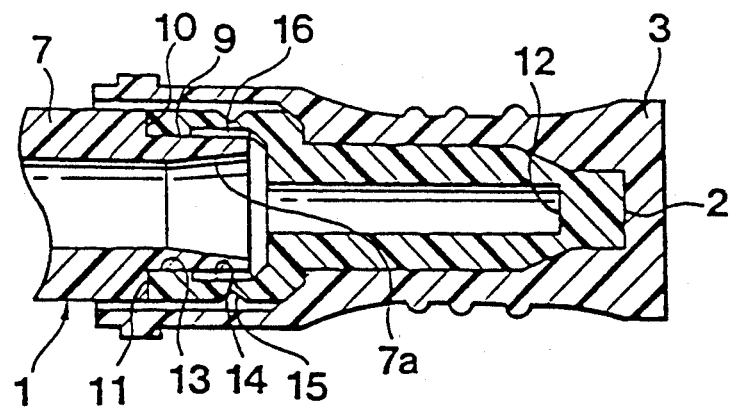

The components are described in detail in FIG. 3a, which is a cross-sectional view of the branch defining the fourth opening 7, the plug 2, and the protector 3 in an exploded state. A full assembly of these components is shown in FIG. 3b. The branch of the four-way branch tube has a flow path-defining bore 7 terminating at an open end and includes a distal wall portion 9 having a smaller outside diameter than the remaining. A step 10 is formed between the distal wall portion 9 and the remaining. The outside wall of the branch is stepped to form the smaller outside diameter wall portion 9 for mounting the plug 2 thereon. The bore 7 of the branch is Luer tapered at 7a.

The tubular body 1 is formed of a relatively rigid material such as polycarbonate. Since the breakable closure member 8 is integrally formed with the tubular body within the third opening 6, formation of the tubular body and the closure member from a rigid material makes it easy to tear off the closure member. The use of a rigid material is also useful to connect a male Luer connector to the branch from which the plug 2 has been torn off for cell return purpose. If the tubular body were formed of a flexible material other than polycarbonate, it would be deformed during autoclave sterilization so that the Luer taper 7a might diminish.

Figures 2A, 2B:
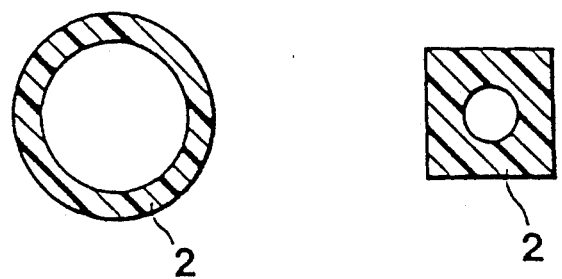
FIG. 2a is an exploded cross-sectional view of the tube assembly of the present invention showing a tube branch, a plug and a protector in a disassembled state.
FIG. 2b is a cross-sectional view of the tube assembly showing a tube branch, a plug and a protector in an assembled state.

The plug 2 includes a hollow mount segment providing an open end 11 at one end and a closing segment axially connected to the mount segment and providing a closing end 12 at another end. The hollow mount segment includes a first wall portion 13 with a relatively smaller inner diameter extending from the open end 11 and a second wall portion 14 with a relatively larger inner diameter extending from the first wall portion 13 to the closing segment. The first wall portion 13 is fixedly secured to the distal wall portion 9 of the branch defining the bore 7 as shown in FIG. 2b. The closing segment may be either a solid segment (not shown) or a hollow segment as shown in FIG. 2a as long as it provides a closing end to the bore of the hollow mount segment. The sum of axial length of the first and second wall portions 13 and 14 of the plug 2 is at least equal to, preferably greater than the axial length of the distal wall portion 9 of the branch defining the bore 7 to ensure firm attachment between the branch and the plug and allow easy tearing of the plug at a frangible portion.

The plug 2 is provided with a frangible portion in the form of a circumferential notch 15 in the outer surface whereby the plug is breakable at the frangible portion and removable from the tubular body or branch. The frangible portion 15 is located such that when the plug 2 is engaged and secured to the distal wall portion 13 of the branch defining the fourth opening 7, the frangible portion is spaced apart from the secured portion. Namely, the frangible portion 15 is located in the second wall portion 14 having a larger inner diameter. In other words, the distal wall portion 9 of the branch axially extends beyond the frangible portion 15 of the plug 2 toward the closing segment. Then the open end of the distal wall portion 9 of the branch is exposed when the plug 2 is torn off. It is then very easy to connect another member having a needle to the protruding open end 9 of the branch. The protruding end of the branch minimizes the possibility of the other member contacting the cut edge of the plug kept attached on the distal wall portion 9 which might be contaminated, avoiding contamination of the flow path of the tubular body 1.

According to the present invention, the material of which the plug 2 is made has a Shore A hardness in the range between 68 and 76, preferably between 74 and 76. Shore A hardness used herein is one scale of durometer hardness applied to represent the hardness of relatively flexible plastics as prescribed by the American National Standard, ASTM D2240-75.

As previously described, the tubular body 1 is made of a relatively rigid material such as polycarbonate. Then the portion of the plug 2 which is attached to the hard tubular body 1 serves as a support so that a tearing force applied to the plug by fingers does not disperse, but concentrates at the frangible portion 15 to facilitate breakage thereof. Nevertheless, an external force other than the carefully applied folding force by fingers is absorbed by the plug 2 which itself is of flexible material and not directly applied to the frangible portion, minimizing the risk of the plug being accidentally broken at the frangible portion.

The plug 2 having a Shore A hardness of less than 68 is too soft so that it can be bent, but is difficult to break.

Experimental data are shown below. Test pieces having the same structure as the plug disclosed in U.S. Pat. No. 3,368,560 were prepared from materials having varying hardness and measured for tensile strength and flexural strength at rupture. The results are shown in Table 1. Tensile strength and flexural strength were measured at a pulling rate of 10 mm/min. and 20 mm/min. and reported as an average of ten and five measurements, respectively.

TABLE 1

| Sample | Shore A | Tensile strength | Flexural strength |
|---|---|---|---|
| 1 | 64–68 | 3.9 kg | unmeasurable |
| 2 | 68–70 | 4.0 kg | unmeasurable |
| 3 | 74–76 | 4.9 kg | unmeasurable |
| 4 | 90–92 | 9.7 kg | 2.5 kg |
| 5 | 98–100 | 16.4 kg | 6.8 kg |

It is seen from Table 1 that those test pieces of material having a Shore A hardness of from 64 to 76 cannot be ruptured by bending.

Test pieces of the plug according to the present invention as shown in FIG. 2a were prepared from materials having varying hardness and measured for tensile strength and flexural strength at rupture. The results are shown in Table 2. Tensile strength and flexural strength were measured at a pulling rate of 20 mm/min. and 50 mm/min. and reported as an average of ten and five measurements, respectively.

TABLE 2

| Sample | Shore A | Tensile strength | Flexural strength |
|---|---|---|---|
| 6 | 68–70 | 4.7 kg | 3.9 kg |
| 7 | 74–76 | 7.0 kg | 3.8 kg |

TABLE 2-continued

| Sample | Shore A | Tensile strength | Flexural strength |
|--------|---------|------------------|-------------------|
| 8 | 87-92 | 10.2 kg | 5.7 kg |

It is seen from Table 2 that plugs having a Shore A hardness of 68 to 76 can be more easily ruptured by bending than plugs having a Shore A hardness of 87 to 92.

The plug preferably has a cross sectional shape other than a circle on a distal side with respect to the frangible portion 15. FIGS. 2a and 2b are cross sections taken along lines A—A and B—B in FIG. 3a, respectively. More particularly, the first wall portion 13 of the plug 2 with a relatively smaller inner diameter which is to be secured to the distal wall portion 9 of the branch defining the bore 7 has substantially a true circular cross section, as shown in FIG. 3a having an inner diameter substantially equal to the outer diameter of the distal wall portion 9. The remaining portion of the plug 2, preferably the closing segment has a non-circular cross section in a direction transverse to an axial direction. For example, the closing segment has a square cross section as shown in FIG. 2b. Since the closing segment is a distal segment of the plug which not only closes the bore in the hollow mount segment, but also serves as a handle or lever upon breaking the plug at the frangible portion, the closing segment may have a rectangular, ellipsoidal or other cross section which is convenient to manually grip.

The tube assembly of the present invention also includes the protector 3 to be fitted over the plug 2. The protector 3 is in close fit with the outside of the plug 2 for protecting the plug. In the example of FIGS. 2a and 2b the protector 3 is a grip which defines therein a cavity having an open end and a closed end. An inside portion of the cavity mates with the closing segment of the plug 2. The shape of the protector 3 is not limited to that shown in FIG. 3a and the protector may be a tubular sleeve having a portion to be tightly engaged over the closing segment of the plug 2.

In order that the plug 2 be readily torn off by grasping and twisting the protector 3, the protector 3 preferably has a non-circular outer configuration such as a rectangular, square and ellipsoidal cross section in a direction transverse to an axial direction.

FIG. 2b shows the components in an assembled state. The plug 2 is mounted on the branch to close its opening 7 and also covered with the protector 3. The first wall portion 13 of the plug is in snug fit over the distal wall portion 9 of the branch. A space 16 is left between the second wall portion 14 of the plug and the distal wall portion 9 of the branch in a radial direction. The space 16 is sufficient to keep the open end of the branch 4 from obstructing in breaking of the plug 2 at the frangible portion 15. For the same reason, the distal or open end of the branch 7 is axially spaced apart from the plug 2.

The protector 3 must be in snug fit over the plug 2 in order to protect the plug 2 from any accidental external force and to prevent any sliding motion between the protector and the plug when the protector 3 is twisted with a finger grip to tear off the plug 2. The protector is in close fit on the closing segment of the plug 2, but axially extends over the frangible portion 15 with a spacing from the mount segment in a proximal direction. A space is left between the inside wall of the protector 3 and the outside wall of the plug 2 at least in a region axially located on the proximal side with respect to the frangible portion 15. In the embodiment shown in FIG. 2b, a space is left between the protector 3 and the mount segment of the plug 2, and the protector 3 is in tight engagement with the closing segment of the plug 2. The space between the inside wall of the protector 3 and the outside wall of the plug 2 bridging over the frangible portion 15 is effective in facilitating separation of the plug 2 by tearing it off.

The fourth opening 7 is closed with the plug 2 covered with the protector 3 when the corresponding branch is not in use. When it is desired to connect another member to the fourth opening 7, the plug 2 is removed from the opening by tearing or twisting off the plug 2 at the frangible portion 15. The fourth opening-defining branch with its flow path open is now ready for connection to another member.

The frangible portion 15 may be formed at any location between the open end 11 and the closed end 12 of the plug. Preferably, the frangible portion 15 is provided in the outside wall of the second or larger inner diameter wall portion 14 of the mount segment of the plug 2. Location of the frangible portion 15 in the second wall portion 14 means that the frangible portion 15 is located radially outside the space 16 between the plug 2 and the branch 7. Then it is very easy to tear off the plug 2 by twisting even though the plug is made of a relatively flexible material.

The engagement between the plug 2 and the protector 3 is not particularly limited as long as it ensures clipping-off of the plug by grasping the protector 3 with fingers and turning it with the plug 2 so as to tear off the plug without any sliding motion between the protector and the plug.

In general, medical tubings are made of polycarbonate and flexible vinyl chloride resin. When a plug is secured to such a tube, it is desired not to use an adhesive at the connection between the plug and the tube in order to avoid contamination to fluid to be passed therethrough, typically blood. If a tube and a plug are made of similar types of material, a blocking bond can be achieved between them by utilizing the heat applied for autoclave sterilization. Since the plug is formed of a relatively flexible material such as polyvinyl chloride resin, it is difficult to tear off the plug with a click by twisting because the plug as a whole is softly twisted. The protector 3 is preferably made of a relatively rigid material in order to facilitate breakage of the plug 2. A choice of the material of the protector 3 is made such that the protector may not be bonded to the branch and the plug through blocking under the influence of the heat applied during autoclave sterilization. A typical example of the relatively rigid material is a polypropylene resin. A preferred combination of materials meeting the above requirement is a combination of polycarbonate for the branch 7 or tubular body, polyvinyl chloride for the plug 2 and polypropylene for the protector 3. Another preferred combination of materials for the tubular body, plug and protector will occur to those skilled in the art in light of the above teachings.

Figure 5:
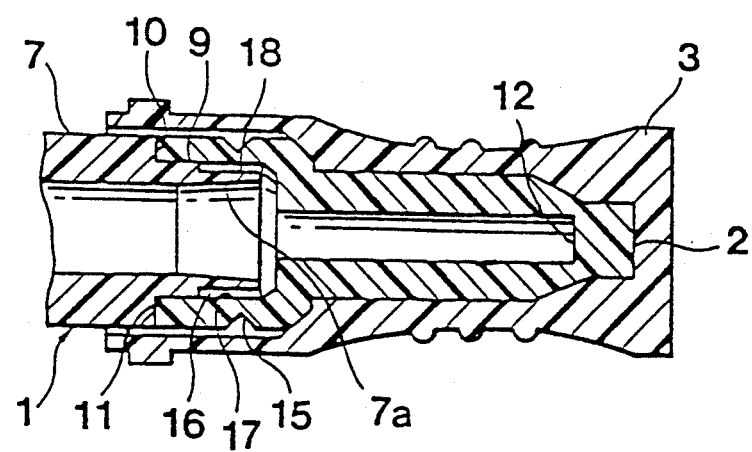
FIG. 5 is a cross-sectional view of a four-way branch tube with a breakaway plug according to another embodiment of the present invention.
Figure 1:
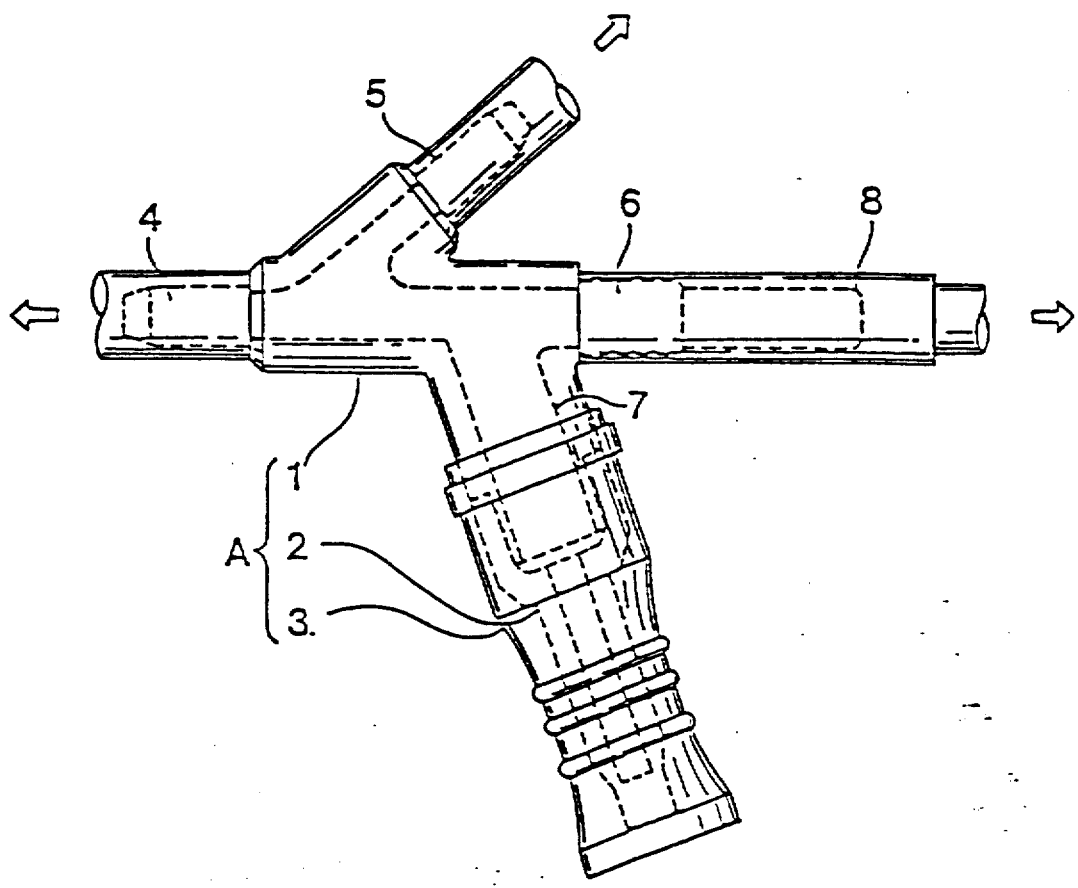
Figures 3A, 3B:
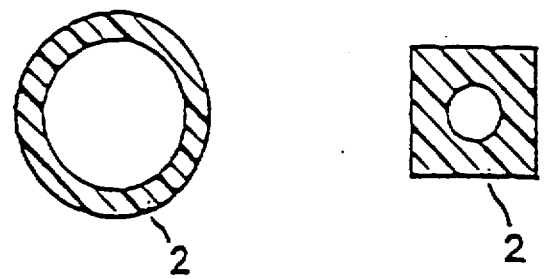

Also, in the present invention, a space 16 may be provided between an inner wall portion of the plug 2 and a reduced diameter portion 9 of the opening 7. As illustrated in FIG. 5, on the reduced diameter portion 9 of the fourth opening 7 in place of on an inner wall portion 17 of the plug 2 may be provided a second stepped down or smaller diameter portion 18 to make a space 18 therebetween.

OPERATION

The operation of the four-way branch tube having a plug mounted on one branch as shown in FIG. 1 is described by referring to a system for plasmapheresis therapy having the branch tube incorpoated therein.

As shown in FIG. 4a, the plasmapheresis system includes four sections of tubing connected to the four-way branch tube 1. A first section of tubing extends from a puncture needle 23 placed in the vein of a donor 27 to the first opening 4 of the branch tube for the purpose of blood collection and has a hemostat 28 thereon. A second section of tubing extends from the second opening 5 of the branch tube to a first blood bag 24a and has a hemostat 26 thereon. A third section of tubing extends from the third opening 6 of the branch tube to a second blood bag 24b via a closure member in the form of a click tip 8. A fourth section of tubing extends from the fourth opening 7 of the branch tube to a Y set 20. The fourth section of tubing is a trunk line of the Y set which includes a first inlet line extending to a physiological saline bottle 22 through a clamp 21a and a second inlet line 30 having a clamp 21b. This is an outline of the system, and all the lines are not connected at the same time. Connection will become apparent from the following description of operation.

While clamps 21a, 21b and 21c on the lines associated with the Y set 20 are closed, a needle connected to the line with clamp 21a is punctured into the saline bottle 22. Then the clamp 21a is opened and the clamp 21b is released to fill the Y set with saline. The clamp 21a is again closed.

During this operation, the plug 2 on the branch 7 of the four-way branch tube is kept normal or unbroken and covered with the protector 3. There is no possibility that the plug is accidentally ruptured to allow contamination of the opening 7 of the branch during manufacture and setting of the branch tube 1. The first opening 4 of the branch tube 1 is in fluid communication with the needle 23, and the second opening 5 in fluid communication with the first blood bag 24a. The third opening 6 is connected to the second blood bag 24b although the click tip 8 is also kept normal or unbroken so that the flow path to the second blood bag 24b is closed.

The next step is to connect a connector at the free end of the Y set trunk to the branch (7) of the branch tube. The hemostat 26 is fastened on the second section of tubing connected to the first blood bag 24a in order to prevent reverse flow of medical liquid in the first blood bag 24a. Then the plug 2 is torn off at the frangible portion 15 to open the associated branch (7) by manually holding and twisting the protector 3. According to the present invention, the plug 2 is made of material having a Shore A hardness of 68 to 76 and the tubular body 1 is made of a relatively rigid material such as polycarbonate. The first wall portion 3 of the plug is fixedly secured to the tubular body 1. Since the tubular body assists in the first wall portion of the plug serving as a rigid support for the plug, a bending force applied to the plug by fingers concentrates at the frangible portion 15. Thus the plug can be readily ruptured at the frangible portion 15 even though the plug is made of material having a relatively low degree of hardness. In addition, the fact that the plug is made of a relatively flexible material provides the advantage that the plug is resistant against rupture by an accidental external force.

After rupture of the plug, the fourth opening 7 is protruded and exposed without damage. Then the opening is easy to connect another member thereto and free of contamination. Easier connection is expected when the fourth opening 7 has the Luer taper 7a or an axially outwardly divergent bore.

Further, in the embodiment wherein the plug 2 is received in the protector 3 of rigid material, the protector in tight engagement over the plug 2 prevents deformation of the plug and assists in tearing off the plug at the frangible portion when the protector 3 is gripped and twisted.

The next step is to collect blood from the donor 27. The first section of tubing is fastened by the hemostat 28 at a location near the needle 23. The puncture needle is inserted into the vein of the donor 27. After entry of blood into the blood collecting tube is observed, the hemostats 28 and 26 are taken off to communicate an open continuous flow path to the first blood bag 24a.

Since the flow path to the second blood bag 24b is closed by the click tip 8 at this point, blood flows under gravity from the needle 23 to the first blood bag 24a. Blood collection is continued until the first blood bag 24a is filled with a predetermined volume of blood. Then the section of tubing to the first blood bag 24a is sealed with a tube sealer or a pair of aluminum rings (not shown) and cut therebetween to separate the first blood bag 24a.

Figure 4B:
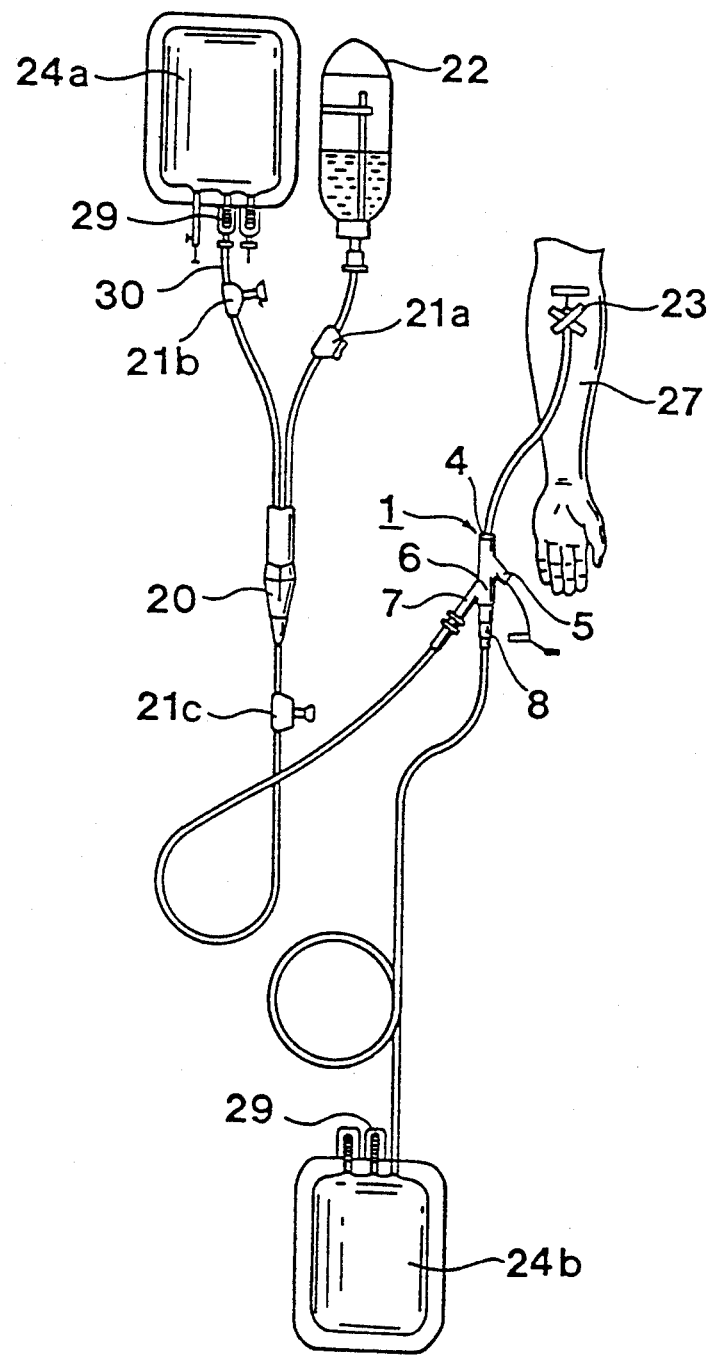

The whole blood in the first blood bag now removed is centrifugally separated into cell and plasma components. During the step, saline is transfused dropwise from the bottle 22 to the donor through the Y set 20, the branch (7) with the plug broken, and the needle 23 as shown in FIG. 4b.

The cells thus separated are return transfused to the donor 27. More particularly, an outlet 29 of the first blood bag 24a is connected to the second inlet tube 30 of the Y set 20. Then the cells are returned along with saline to the donor 27 through the Y set 20, the four-way branch tube 1, and the needle 23.

At the end of return transfusion, the branch tube 1 is held in one hand, and the click tip 8 is manually torn off to open the flow path to the second blood bag 24b. Blood is again collected from the donor 27 to the second blood bag 24b through the needle 23 which has been placed in the vein of the donor. Likewise the first blood bag 24a, the blood collected in the second blood bag 24b is centrifugally separated and transfused back to the donor.

INDUSTRIAL UTILITY OF THE PRESENT INVENTION

In the tube assembly of the present invention, an attachment portion of a plug of a relatively flexible material having a Shore A hardness of 68 to 76 is fixedly secured to a relatively rigid tubular body. The connection between the plug and the tubular body is improved in gas tightness and intimate contact so that the plug is firmly bonded to the tubular body. Then the plug maintains the ability of being ready to be ruptured when the associated tubular body is on use. The risk of the plug being accidentally ruptured by an external force when the tubular body is not in use is minimized. Thus, contamination of the tubular body is prevented when it is not in use.

I claim:

1. A tube assembly comprising:

a tubular body of a relatively rigid material having at least two open ends, a plug of a material having a Shore A hardness of from 68 to 76 mounted on one open end of said tubular body, said plug including (a) a hollow mount segment having an open end, a portion of the mount segment extending from its open end being fixedly secured to the one open end of said tubular body, (b) a closing segment axially connected to the mount segment, (c) a frangible portion located axially outside the secure portion whereby said plug is breakable at the frangible portion and removable from the one open end of the tubular body; and (d) a protector fitted over the plug.

* * * * *

UNITED STATES PATENT AND TRADEMARK OFFICE
CERTIFICATE OF CORRECTION

PATENT NO. : 5,152,755

DATED : October 6, 1992

INVENTOR(S) : YOSHINORI, MINAGAWA

Figure 2A:
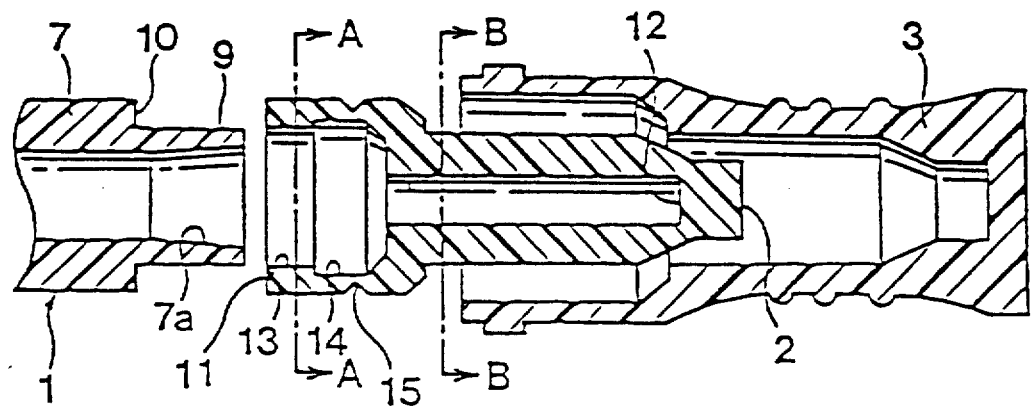
Figure 2B:
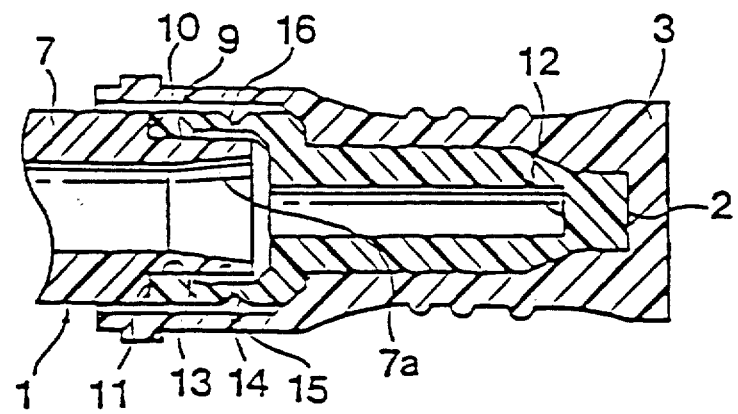

It is certified that error appears in the above-identified patent and that said Letters Patent is hereby corrected as shown below:

Sheet 1 and 2 of the drawings, consisting of Figs. 1 and 2, should be deleted to be replaced with the sheet of drawings, consisting of Fig. 1-2, as shown on the attached page.

Signed and Sealed this

Sixteenth Day of November, 1993

*Attest:*

BRUCE LEHMAN

*Attesting Officer*   *Commissioner of Patents and Trademarks*